(12) United States Patent
Lu et al.

(10) Patent No.: US 11,847,786 B2
(45) Date of Patent: Dec. 19, 2023

(54) MOTION LEARNING WITHOUT LABELS

(71) Applicant: EchoNous, Inc., Redmond, WA (US)

(72) Inventors: Allen Lu, Seattle, WA (US); Babajide Ayinde, Redmond, WA (US)

(73) Assignee: ECHONOUS, INC., Redmond, WA (US)

( * ) Notice: Subject to any disclaimer, the term of this patent is extended or adjusted under 35 U.S.C. 154(b) by 267 days.

(21) Appl. No.: 17/316,336

(22) Filed: May 10, 2021

(65) Prior Publication Data

US 2021/0350549 A1 Nov. 11, 2021

Related U.S. Application Data

(60) Provisional application No. 63/022,989, filed on May 11, 2020.

(51) Int. Cl.
*G06T 7/269* (2017.01)
*G06T 7/215* (2017.01)
(Continued)

(52) U.S. Cl.
CPC ............ *G06T 7/269* (2017.01); *A61B 8/0883* (2013.01); *A61B 8/485* (2013.01); *G06F 18/213* (2023.01); *G06F 18/2155* (2023.01); *G06F 18/2178* (2023.01); *G06N 20/00* (2019.01); *G06T 7/11* (2017.01); *G06T 7/149* (2017.01); *G06T 7/168* (2017.01); *G06T 7/215* (2017.01); *G06T 7/30* (2017.01); *G06V 10/778* (2022.01); *G06V 10/82* (2022.01); *G16H 30/20* (2018.01); *G06T 2207/10132* (2013.01); *G06T 2207/20081* (2013.01); *G06T 2207/20084* (2013.01); *G06T 2207/30048* (2013.01)

(58) Field of Classification Search
CPC . G06T 7/269; G06T 7/11; G06T 7/149; G06T 7/168; G06T 7/215; G06T 7/30; G06T 2207/10132; G06T 2207/20081; G06T 2207/20084; G06T 2207/30048; G06T 2207/10016; A61B 8/0883; A61B 8/485; A61B 8/5276; G06F 18/213; G06F 18/2155; G06F 18/2178; G06N 20/00; G06N 3/045; G06N 3/084; G06V 10/778; G06V 10/82; G06V 2201/031; G16H 30/20; G16H 30/40
See application file for complete search history.

(56) References Cited

U.S. PATENT DOCUMENTS

2013/0116739 A1\* 5/2013 Brada .................... A61B 6/486
600/431
2018/0124425 A1 5/2018 Van Leuven et al.
(Continued)

OTHER PUBLICATIONS

International Search Report and Written Opinion, dated May 10, 2021, for International Application No. PCT/US2021/031618, 11 pages.
(Continued)

*Primary Examiner* — Jianxun Yang
(74) *Attorney, Agent, or Firm* — SEED IP LAW GROUP LLP

(57) ABSTRACT

A machine learning model is described that is trained without labels to predict a motion field between a pair of images. The trained model can be applied to a distinguished pair of images to predict a motion field between the distinguished pair of images.

26 Claims, 8 Drawing Sheets

(51) Int. Cl.

| | |
|---|---|
| G16H 30/20 | (2018.01) |
| G06T 7/168 | (2017.01) |
| G06T 7/11 | (2017.01) |
| G06T 7/149 | (2017.01) |
| G06T 7/30 | (2017.01) |
| A61B 8/08 | (2006.01) |
| G06N 20/00 | (2019.01) |
| G06F 18/213 | (2023.01) |
| G06F 18/214 | (2023.01) |
| G06F 18/21 | (2023.01) |
| G06V 10/778 | (2022.01) |
| G06V 10/82 | (2022.01) |

(56) References Cited

U.S. PATENT DOCUMENTS

2019/0205766 A1* 7/2019 Krebs ............... G06F 18/2413
2021/0166065 A1* 6/2021 Chang ................. G06T 7/0002

OTHER PUBLICATIONS

Guo et al., "A Spatiotemporal Volumetric Interpolation Network for 4D Dynamic Medical Image," *Institute for Medical Imaging Technology*:4321-4330, 2020.

Ouzir et al., "Motion Estimation in Echocardiography Using Sparse Representation and Dictionary Learning," *IEEE Transactions on Image Processing*. 27(1):64-77, 2017.

Lee et al., "Instance-wise Depth and Motion Learning from Monocular Videos," arXiv:1912.09351 v2. Apr. 8, 2020. Retrieved from https://arxiv.org/pdf/1912.09351.pdf. 16 pages.

D'hooge et al., "Regional Strain and Strain Rate Measurement by Cardiac Ultrasound: Principles, Implementation and Limitations", *European Journal of Echocardiography*. 1(3):154-170, 2000.

Dahl et al., "Early Diastolic Strain Rate in Relation to Systolic and Diastolic Function and Prognosis in Aortic Stenosis," *Elsevier*. 9(5):519-528, 2016.

Kasner et al., "Global Strain Rate Imaging For The Estimation Of Diastolic Function In HFNEF Compared With Pressure-Volume Loop Analysis," *European Journal of Echocardiography*. 11(9): 743-751, 2010.

Smiseth et al., "Myocardial strain imaging: how useful is it in clinical decision making?," *European Journal of Echocardiography*. 37(15): 1196-1207, 2016.

Ta et al., "A Semi-Supervised Joint Learning Approach To Left Ventricular Segmentation And Motion Tracking in Echocardiography," *IEEE 17th International Symposium on Biomedical Imaging*, Iowa City, Iowa, USA, Apr. 3-7, 2020, pp. 1734-1737.

Wang et al., "Global Diastolic Strain Rate for the Assessment of Left Ventricular Relaxation and Filling Pressures," *Circulation*. 115(11):1377-1383, 2007.

* cited by examiner

MOTION LEARNING WITHOUT LABELS

CROSS-REFERENCE TO RELATED APPLICATIONS

This application claims the benefit of 63/022,989, filed May 11, 2020 and entitled "MOTION LEARNING WITHOUT LABELS," which is hereby incorporated by reference in its entirety.

In cases where the present application conflicts with a document incorporated by reference, the present application controls.

BACKGROUND

Strain measures an object's deformation relative its original shape. FIG. 1 shows an example of 1-dimensional deformation of an object. Force is applied to the object 110 to increase its initial length Lo 111 to a distended length L 121, resulting in deformed object 120.

Equation (1) below determines the one-dimensional strain for this example.

$$\varepsilon = \frac{L - L_0}{L_0} \qquad (1)$$

One-dimensional strain has only 1 component. In three-dimensional medical imaging, such as ultrasound imaging, it is common to assess two-dimensional or three-dimensional strain, which have 2 components or 3 components, respectively. Clinicians typically project cardiac strain into 3 clinically-relevant directions.

FIG. 2 shows three directions in which cardiac strain is commonly projected. The context is the heart 200, having a wall 202 bounded by an outer surface 201 and an inner surface 203. A section of the heart is shown, comprising a section 212 of wall 202, a section 211 of outer surface 201, and a section 213 of inner surface 203. The three directions in which cardiac strain is commonly projected radially, away from the center of the heart, 221; circumferentially or tangentially, along the surface of the LV, 222; and longitudinally, in the axial direction of the heart, 223.

Strain has the potential to be incredibly useful in the clinical setting. In the paper *Myocardial strain imaging: how useful is it in clinical decision making?*, published in European Heart Journal in 2016, the author described that strain may be useful as a supplementary diagnostic method in the following ways (quoting):

1. In patients with preserved or normal LVEF, reduced GLS may be used to identify systolic dysfunction.
2. Strain imaging can be used to identify sub-clinical LV dysfunction in individuals who are evaluated for cardiomyopathy. This includes family screening for HCM and the finding of reduced GLS indicates early disease.
3. In patients with valvular heart disease reduced GLS reflects negative impact of the valve lesion on myocardial function prior to fall in LVEF, but so far this application is not recommended for use in clinical routine.
4. Strain imaging is recommended in addition to LVEF in patients undergoing chemotherapy to identify sub-clinical LV dysfunction.
5. Strain may be used to diagnose myocardial ischaemia, but the technology is not sufficiently standardized to be recommended as a general tool for this purpose. In unclear clinical cases, however, it may be considered as a supplementary method.
6. Strain imaging may be applied in patients eligible for CRT to guide placement of the LV pacing lead, but is currently not recommended for selection of CRT responders.
7. Peak systolic longitudinal LA strain is a promising supplementary index of LV filling pressure, but needs further validation in prospective trials.

In addition, various other publications have shown global longitudinal strain and various strain rate-derived ratios to be correlated to diastolic dysfunction.

FIG. 3 is a data flow diagram showing a generic workflow for computing strain at a high level. In the workflow 300, motion tracking is performed on a sequence of 2D ultrasound images 301-304 to generate a displacement field 320, which describes the motion of each pixel in the image over the course of the sequence. Concretely, for each image frame in the sequence, there are 2 displacement images, one explains pixel displacement in the X direction, and the other for the Y direction. Strain is computed from the displacement field, and can be shown in various representations, including a 17-segment strain map 331 showing strain at end-systole (ES), strain curves 332 for each segment, strain rate (temporal derivative of strain), and a global strain value. Global longitudinal strain and strain rate (GLS) 3340 are examples of global values evaluated in various studies.

Speckle tracking is a popular motion tracking approach used in clinics today. FIG. 4 shows is a data flow diagram showing a generic workflow for speckle tracking. For each image frame 410, a rectangular Region of Interest (ROI) patch 411 is defined around a pixel of interest. Then, in the subsequent image frame 420, the previous defined ROI patch 411/431 is matched to every possible patch 432-435 in the Search region 421/430. The location of the patch in the Search region that has the highest similarity to the original ROI patch, patch 434/44, is designated as the location where pixel of interested moved to from the original image frame to the subsequent image frame. It is used as a basis for determining vertical motion displacement 446 and horizontal motion displacement 447.

Deformable registration is another popular motion tracking approach but is not yet commonly used in clinics. FIG. 5 shows a generic workflow for deformable registration. Motion is estimated between two images 510 and 520 by deforming/displacing a pre-defined grid 511 on the moving image to obtain deformed-displaced grid 521 that maximizes similarity to the fixed image. The grid points are the parameters of kernels, such as B-splines and thin plate splines, that implicitly spatially smooth the displacement field. This maximization process is solved with a global objective function and is usually solved in a multi-scale framework to mitigate convergence to local maxima.

DETAILED DESCRIPTION

Figure 1:
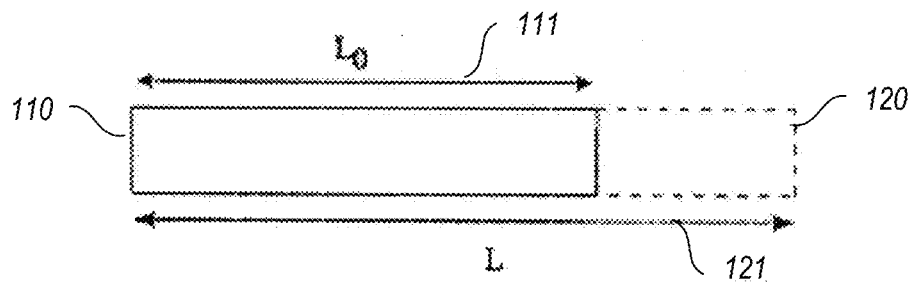
FIG. 1 shows an example of 1-dimensional deformation of an object.
Figure 2:
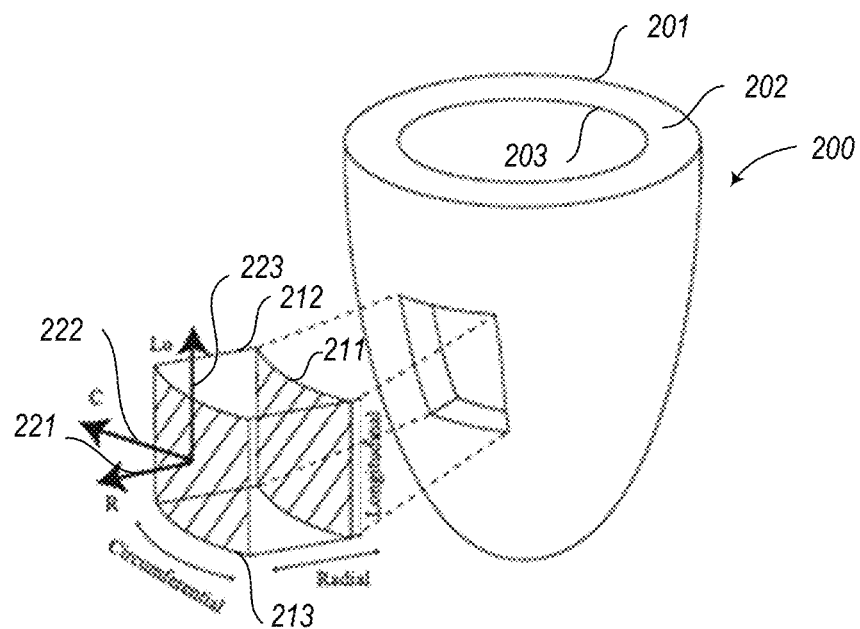
FIG. 2 shows three directions in which cardiac strain is commonly projected.

The inventor has identified significant disadvantages in the conventional approaches to motion tracking. He has recognized that speckle tracking relies on tracking local speckle patterns over the image sequence. As a result, it requires a consistent propagation of speckle over time and requires a high frame-rate/temporal resolution. High temporal resolution necessitates lower spatial resolution, which is an unfortunate trade-off that should be avoided.

The inventor has observed that deformable registration is computationally intensive. Registration of 2-dimensional frames usually takes 10-30 seconds, and this process needs to be repeated for each frame in the image sequence. In addition, it is possible for the optimization to be stuck in a local maximum, which produces lower accuracy and timing.

He has further recognized that both speckle tracking and deformable registration solve large, computationally intensive optimization problems for each pair of images, and for each inference. This consumes significant computing resources for each inference, and results in a sizable latency time for inference.

Also, while it is theoretically possible to train a neural network for this inference using ground-truth displacements, in practice it is difficult to acquire the ground-truth displacements that would be needed, since a displacement label would be needed for each pixel a number of different training data image pairs used to train such a neural network.

In response to recognizing these disadvantages, the inventor has conceived and reduced to practice a software and/or hardware facility that uses deep learning to determine a displacement or velocity field (a "motion field") from a sequence of ultrasound images without using training labels. In various embodiments, the facility uses this displacement or velocity field to compute motion-based clinical measurements such as strain and strain rate from echocardiography.

In some embodiments, the facility trains a neural network using a set of training pairs of radiological images, each pair captured from the same patient at different times. To perform the training, the facility applies the present state of the machine learning model to the images of the training pair to obtain a predicted motion field. The facility applies a spatial transform to transform the first radiological image of the training pair using the predicted motion field, and compares the transformed first radiological image of the training pair to the second radiological image of the training pair to obtain a loss metric value. The facility adjusts adjusting the state of the machine learning model based on the loss metric value, and continues with additional training image pairs until the loss metric value reaches an acceptably low level.

By performing in some or all of the ways described above, the facility can determine a strain assessment rapidly from a patient's video frames—such as in less than one second, permitting it to be acted on promptly—while producing good results, even for large deformations, without the need to determine ground-truth displacements for neural network training.

Also, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. As one example, by reducing the procession burden of inference relative to conventional approaches, the facility permits a computing device used for inference to have a less powerful processor or fewer processors, or be used for additional or different tasks simultaneously.

Figure 6:
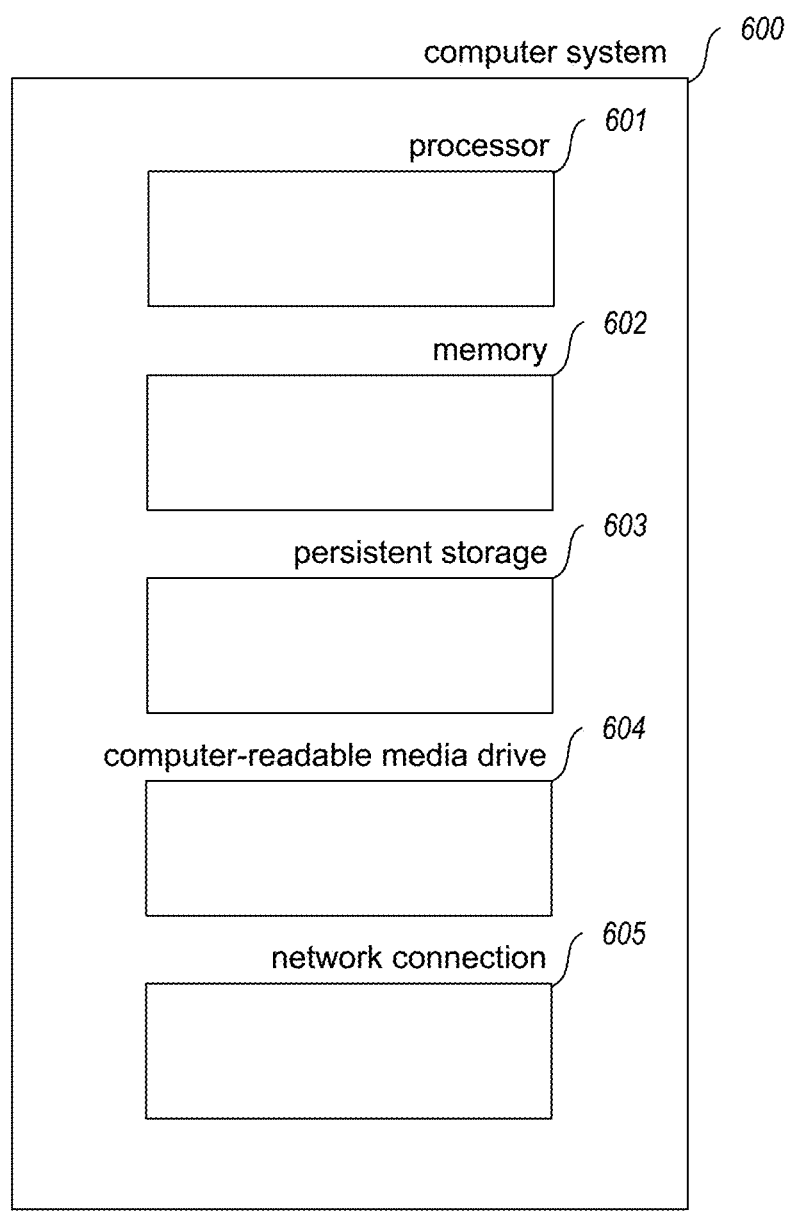
FIG. 6 is a block diagram showing some of the components typically incorporated in at least some of the computer systems and other devices on which the facility operates.

FIG. 6 is a block diagram showing some of the components typically incorporated in at least some of the computer systems and other devices on which the facility operates. In various embodiments, these computer systems and other devices 600 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") or processor of another type 601 for executing computer programs; a computer memory 602 for storing programs and data while they are being used, including the facility and associated data, an operating system including a kernel, and device drivers; a persistent storage device 603, such as a hard drive or flash drive for persistently storing programs and data; a computer-readable media drive 604, such as a floppy, CD-ROM, or DVD drive, for reading programs and data stored on a computer-readable medium; and a network connection 605 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 7:
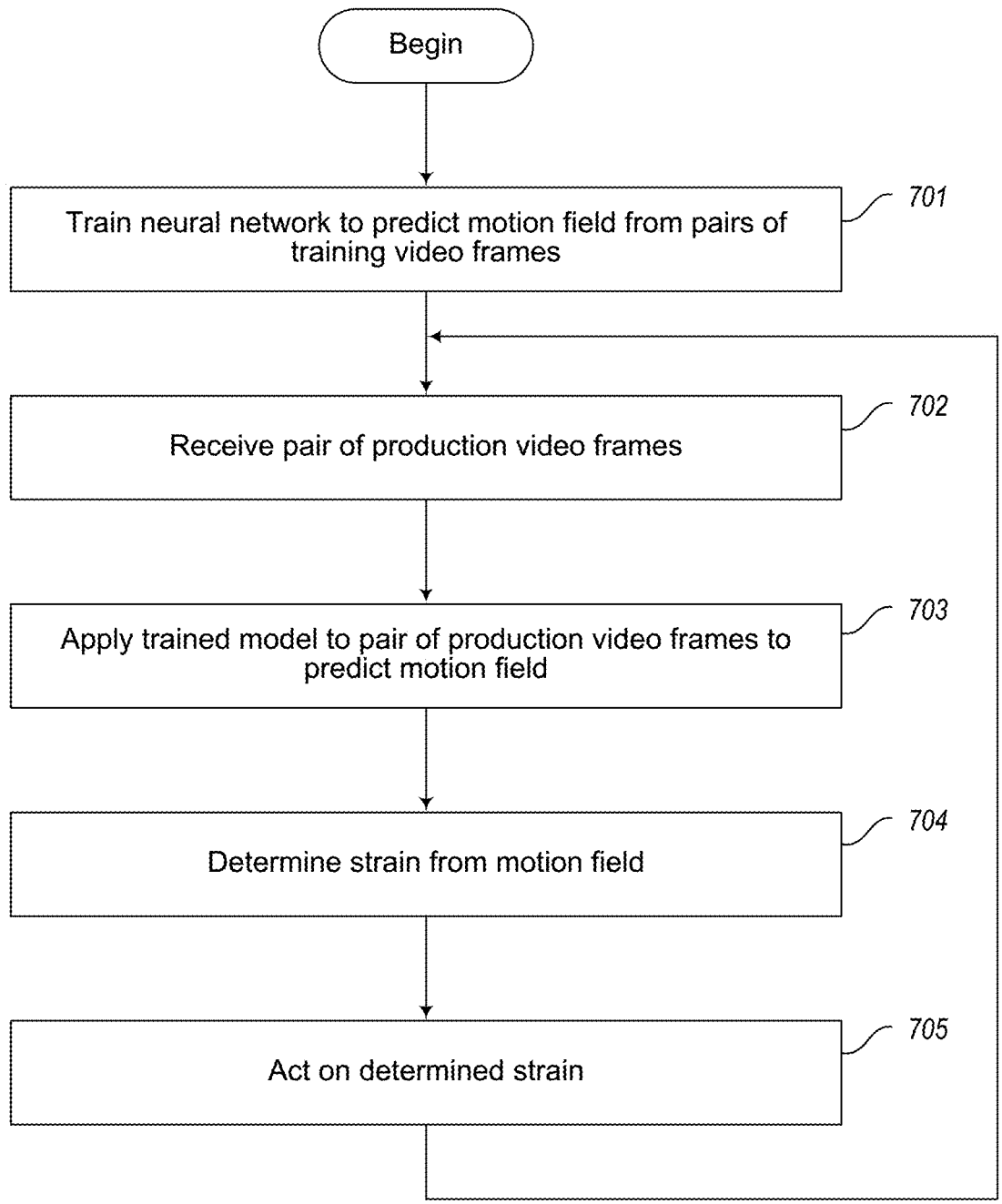
FIG. 7 is a flow diagram showing a process performed by the facility in some embodiments to assess strain based on three-dimensional video.

FIG. 7 is a flow diagram showing a process performed by the facility in some embodiments to assess strain based on three-dimensional video. In act 701, the facility uses many pairs of training video frames to train a neural network to predict a motion field—such as a displacement field or a velocity field—from a pair of production video frames. In various embodiments, the facility uses neural networks of a variety of types. In some embodiments, the facility uses a UNET-based convolutional neural network. In various embodiments, the facility uses various other types of fully-convolutional networks. In some embodiments, the facility uses experimentation to configure the neural network.

Figure 8:
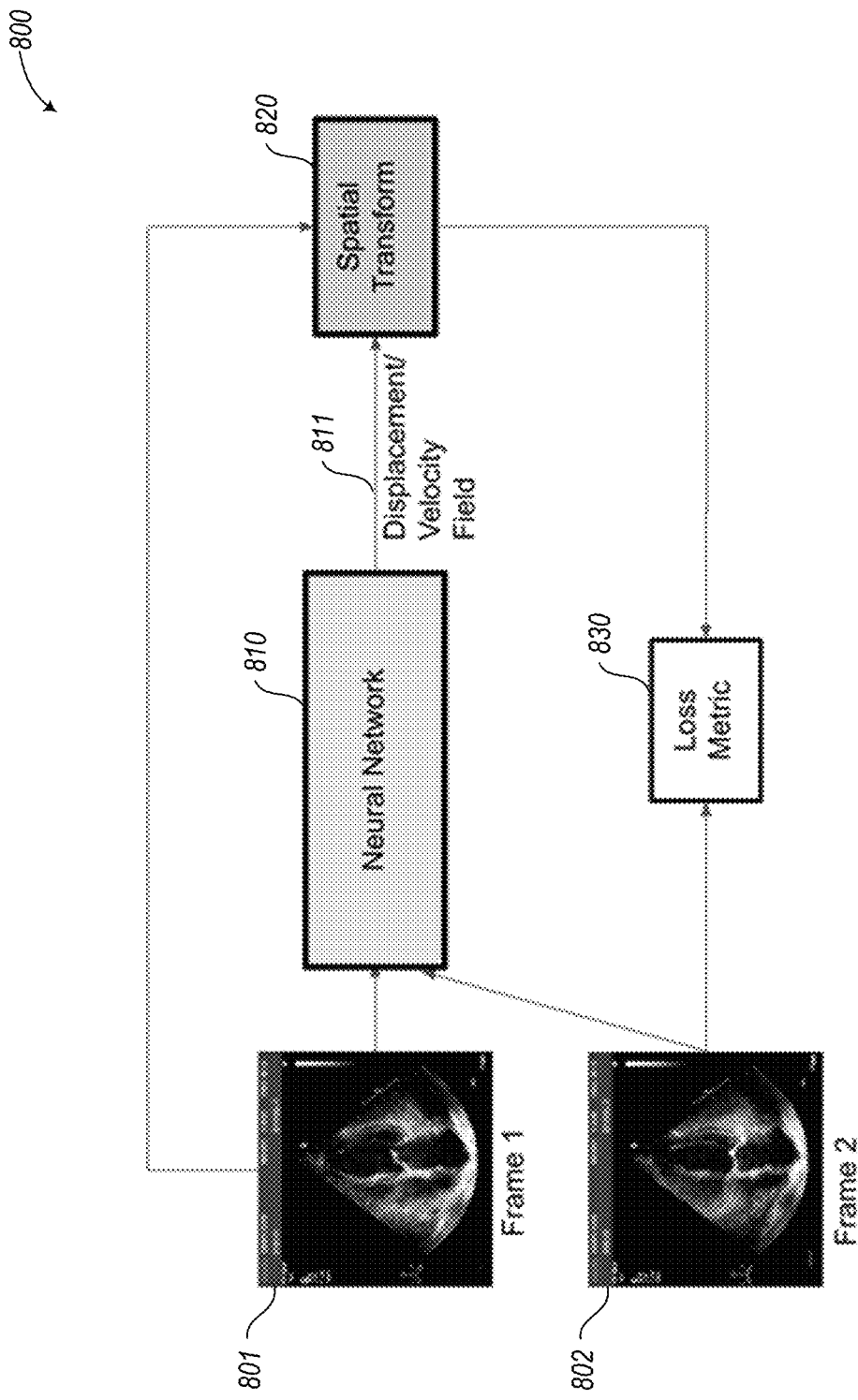
FIG. 8 is a data flow diagram depicting the facility's training of the neural network.

FIG. 8 is a data flow diagram depicting the facility's training of the neural network. The facility feeds two images, Frame 1 801 and Frame 2 802, into the neural network 810 in its present state. The network outputs a displacement or velocity field 811. The facility uses the outputted displacement field to displace 720 a fixed mesh grid from Frame 1, and the displaced mesh grid is used to sample the pixel intensities from transformed Frame 1 for comparison to Frame 2. This comparison produces a Loss Metric 730. The facility uses the Loss Metric adjust the training state of the neural network. The facility repeats this process until the Loss Metric is converges to a minimal value.

Returning to FIG. 7, in act 702, the facility receives a pair of production video frames; i.e., frames from video captured from a patient for which strain is to be assessed. In act 703, the facility applies the neural network trained in act 701 to the received pair of production video frames to predict a motion field for the received pair of production video frames.

Figure 9:
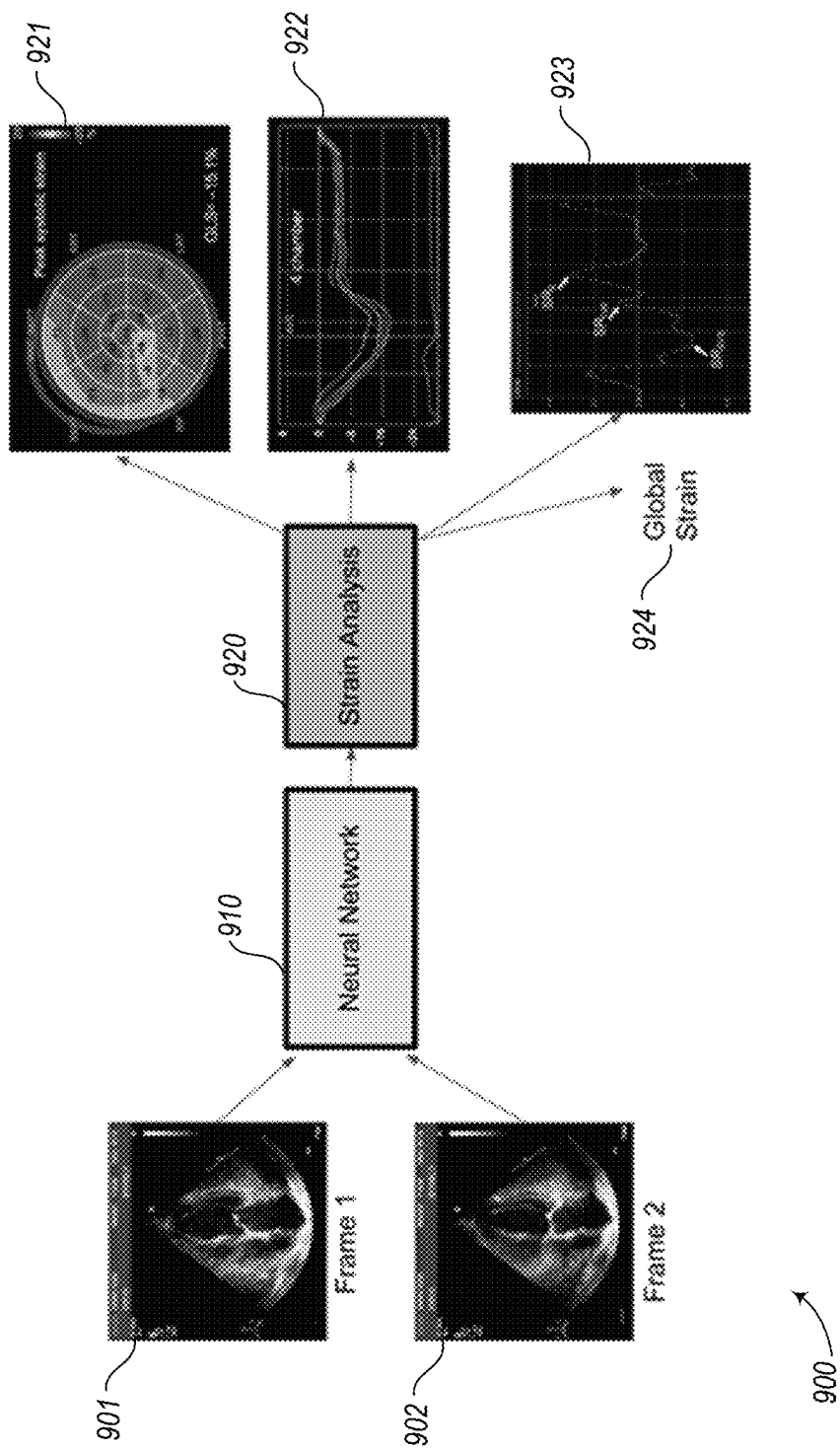
FIG. 9 is a data flow diagram depicting the facility's application of the neural network.

FIG. 9 is a data flow diagram depicting the facility's application of the neural network. The facility subjects production video frame 1 901 and production video frame 2 902 to trained neural network 910 to produce a predicted motion field for the pair of production video frames.

Figure 3:
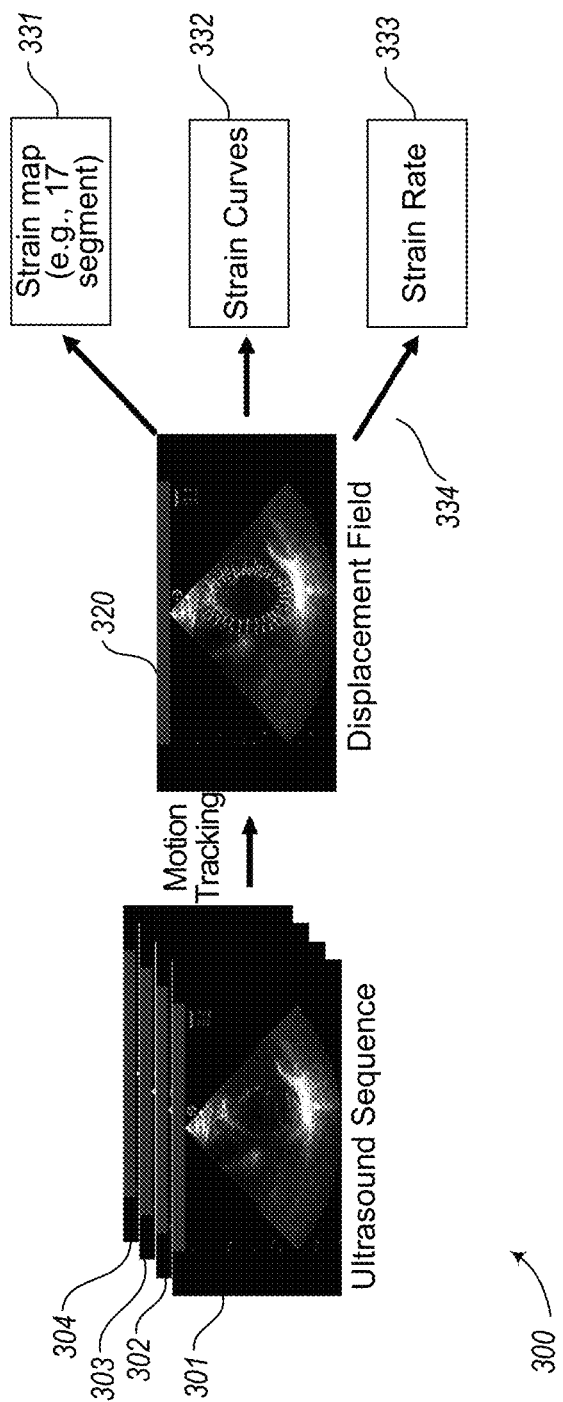
FIG. 3 is a data flow diagram showing a generic workflow for computing strain at a high level.
Figure 4:
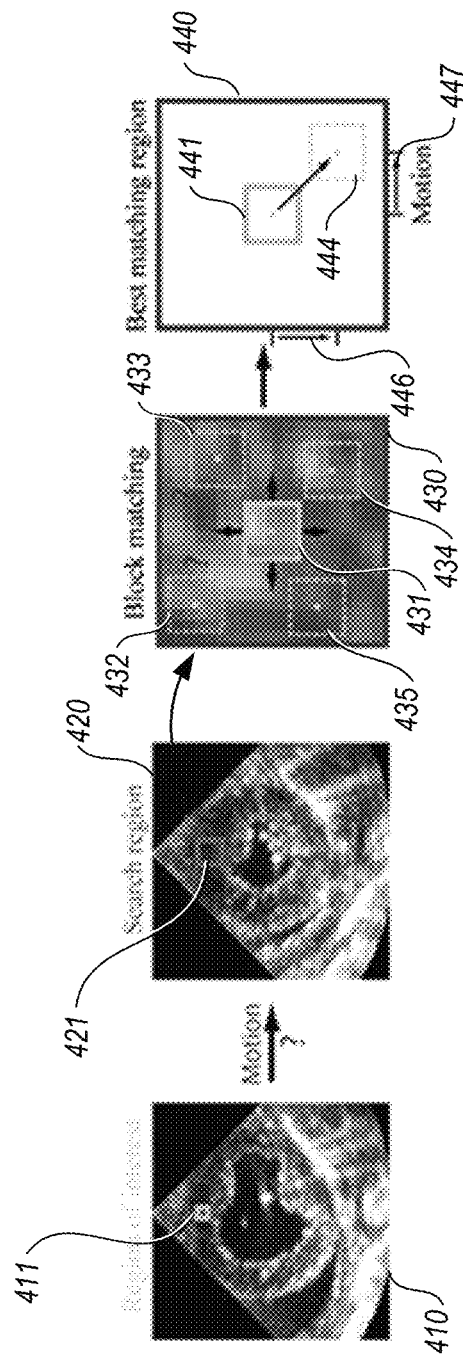
FIG. 4 shows is a data flow diagram showing a generic workflow for speckle tracking.
Figure 5:
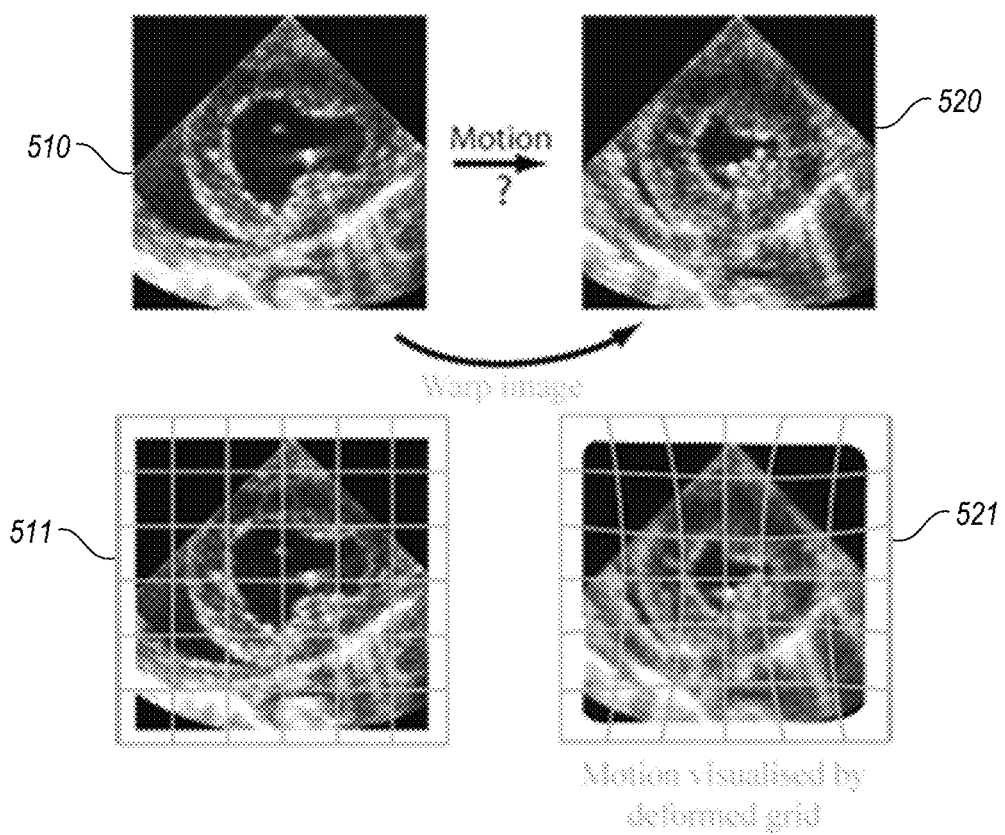
FIG. 5 shows a generic workflow for deformable registration.

Returning to FIG. 7, in act 704, the facility performs strain analysis (shown as analysis 920 in FIG. 9) against the motion field predicted in act 703. This produces one or more of strain representations 921-924 shown in FIG. 9, described above in connection with FIG. 3.

In act 705, the facility acts on the strain determined in act 704. In various embodiments, this includes one or more of storing a produced strain representation on behalf of the patient from whom the production video frames were obtained; displaying storing a produced strain representation; performing diagnostic analysis for the patient based at least in part on a produced strain representation; etc. After act 705, this process continues in step 702 to receive and process the next pair of production video frames.

Those skilled in the art will appreciate that the acts shown in FIG. 7 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

In some embodiments, objective functions of the neural network used by the facility and their optimization are designed in a flexible manner. In some embodiments, custom objective functions and training frameworks can be designed to suit particular ultrasound image sequence analyses.

In various embodiments, the facility uses one or more of the following approaches:

1. Masking the image domain for only the region of interest during training (e.g., myocardium, bounding box of LV), as this allows the network to emphasize producing reliable displacements inside the Region of Interest (ROI), and hence improve the performance of the network. This entails two steps: 1.) a segmentation of the ROI is provided with a prior manual segmentation or segmentation via an automated or semi-automated algorithm. The output of this step is a binary image, where a value of "1" is set for within the ROI, and 0 outside of the ROI. 2.) This mask is applied to the Loss Metric (e.g. pixel-wise multiplication of the mask and the spatially-transformed image) during neural network training. This allows the training to backpropagate gradients of the loss for only the ROI. In some embodiments, the facility jointly trains both the motion tracking network and the segmentation network, as described in K. Ta, S. S. Ahn, A. Lu, J. C. Stendahl, A. J. Sinusas and J. S. Duncan, "A Semi-Supervised Joint Learning Approach to Left Ventricular Segmentation and Motion Tracking in Echocardiography," 2020 *IEEE 17th International Symposium on Biomedical Imaging (ISBI)*, Iowa City, IA, USA, 2020, pp. 1734-1737, available at ieeexplore.ieee.org/abstract/document/9098664, which is hereby incorporated by reference in its entirety.

2. Enforcing diffeomorphic transformation (making sure that the learned displacement field is invertible: $T(A) \rightarrow B$, $T^{-1}(B) \rightarrow A$). The physical intuition is that the learned displacement field should be invertible. In other words, if you apply the learned displacement field on Frame 1 to predict Frame 2, then you can also apply the inverse of the displacement field from Frame 2 to Frame 1. In some embodiments, the facility applies enforcement during the training process, where the inverse of the displacement field is incorporated in the loss to also transform Frame 2 to Frame 1 (in addition to the standard configuration, where the displacement field transforms Frame 1 to Frame 2), and the sum of these two losses are backpropagated to learn the diffeomorphic property.

3. Enforcing consistency of transformation with landmarks, such as contour of LV blood pool. The benefit of this approach is that displacements near the boundaries of the ROI is emphasized during the training process. Similar to point number 1, if you have the mask of the ROI available, then you can also transform the contour of the ROI from Frame 1 to Frame 2 with the learned displacement field. So, if you have manual, semi-automated, or automated algorithm of the segmentation of the ROI available to segment both Frame 1 and Frame 2, then the resulting displacement field can be applied to the ROI contour for Frame 1 and attempt to match to Frame 2, and a contour-based loss can be used to learn this.

4. Predicting a spatiotemporal displacement field that enforces temporal consistency. The benefit of predicting a spatiotemporal displacement field (i.e. over N frames in an image sequence) instead of predicting just a frame-to-frame displacement (over 2 frames in an image sequence) is that a spatiotemporally smooth displacements are produced, which is more physiologically relevant.

5. Using noisy labels, such as results from deformable registration or speckle tracking, to initialize the neural network parameters. In some embodiments, the facility learns this unsupervised learning framework by first training the network using a supervised learning approach (i.e. with labels during training), where the labels are noisy and based on a traditional motion tracking approach, such as non-rigid registration. Then, the facility uses the learned weights from non-rigid registration to restart training in an unsupervised manner. In some cases, this has the benefit of training a higher-performance network with less training data.

In some embodiments, the facility applies approaches discussed above to a variety of other motion abnormality detection applications.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method in a computing system, comprising:
   training a machine learning model to predict the value of a motion field between a pair of radiological images captured from the same patient at different times, by:
   for each of a plurality of training pairs of radiological images captured from the same patient at different times:
   applying the machine learning model to first and second radiological images of the training pair to obtain a predicted motion field value;
   applying a spatial transform to transform the first radiological image of the training pair using the predicted motion field value;
   comparing the transformed first radiological image of the training pair to the second radiological image of the training pair to obtain a loss metric value;
   determining an inverse of the obtained predicted motion field value;
   applying a spatial transform to transform the second radiological image of the training pair using the determined inverse of the predicted motion field value;
   comparing the transformed second radiological image of the training pair to the first radiological image of the training pair to obtain an additional loss metric value; and
   adjusting the state of the machine learning model based on a sum of the loss metric value and the additional loss metric value; and
   storing the trained state of the machine learning model.

2. The method of claim 1 wherein the motion field predicted by the trained machine learning model is a displacement motion field.

3. The method of claim 1 wherein the motion field predicted by the trained machine learning model is a velocity motion field.

4. The method of claim 1 wherein the machine learning model is a neural network.

5. The method of claim 1 wherein the machine learning model is a UNET-based convolutional neural network.

6. The method of claim 1 wherein the radiological images are ultrasound images.

7. The method of claim 1 wherein the radiological images are cardiac ultrasound images.

8. The method of claim 1, further comprising, for each of the plurality of training pairs:
   generating a segmentation mask against the first and second radiological images; and
   before the adjusting, applying the mask to the obtained loss metric value.

9. The method of claim 1, further comprising:
   for each of the plurality of training pairs:
   determining a region of interest segmentation mask against the first and second radiological images of the training pair;
   applying a contour transform to transform the first radiological image of the training pair using the predicted motion field value and the region of interest segmentation mask; and
   comparing the contour-transformed first radiological image of the training pair to the second radiological image of the training pair to obtain a contour loss metric value, and wherein the adjusting adjusts the state of the machine learning model based on the loss metric value and the contour loss metric value.

10. The method of claim 1 wherein the training is performed for training pairs of radiological images taken from a sequence of three or more radiological images captured from the same patient at different times.

11. The method of claim 1 wherein the training is performed after initializing the machine learning model using a supervised learning approach in which labels are noisy.

12. The method of claim 11 wherein non-rigid registration is used in the initialization.

13. The method of claim 1, further comprising:
   receiving a production pair of radiological images captured from a distinguished patient at different times;
   applying the trained state of the machine learning model to the production pair of radiological images to produce a predicted motion field value for the production pair of radiological images; and
   determining a strain result for the distinguished patient using the predicted motion field value for the production pair of radiological images.

14. One or more computer memories not constituting a carrier wave per se and collectively containing a machine learning model data structure, the data structure comprising:
   information representing a machine learning model trained without labels to predict a motion field between a pair of images, the representation of the machine learning model having been trained by, for each of a plurality of training pairs of radiological images captured from the same patient at different times;
   determining an inverse of the obtained predicted motion field value;
   applying a spatial transform to transform the second radiological image of the training pair using the determined inverse of the predicted motion field value;
   comparing the transformed second radiological image of the training pair to the first radiological image of the training pair to obtain an additional loss metric value; and
   adjusting the state of the machine learning model based on a sum of the loss metric value and the additional loss metric value,
   such that the contents of the data structure are usable to instantiate the trained model for application to a distinguished pair of images to predict a motion field between the distinguished pair of images.

15. The one or more computer memories of claim 14 wherein the motion field is a displacement field.

16. The one or more computer memories of claim 14 wherein the motion field is a velocity field.

17. The one or more computer memories of claim 14 wherein the distinguished pair of images are radiological images captured at different times from the same patient.

18. The one or more computer memories of claim 14 wherein the trained machine learning model represented by the data structure's contents is a fully-convolutional neural network.

19. The one or more computer memories of claim 18 wherein the trained machine learning model represented by the data structure's contents is a UNET-based convolutional neural network.

20. The one or more computer memories of claim 14 wherein the trained machine learning model represented by the data structure's contents was trained by:
for each of a plurality of training pairs of images:
applying the machine learning model to first and second images of the training pair to obtain a predicted motion field;
applying a spatial transform to transform the first image of the training pair using the predicted motion field;
comparing the transformed first image of the training pair to the second image of the training pair to obtain a loss metric value; and
adjusting the state of the machine learning model based on the loss metric value.

21. One or more instances of computer-readable media not constituting a carrier wave per se and collectively having contents configured to cause a computing system to perform a method, the method comprising:
receiving a production pair of radiological images captured from a distinguished patient at different times;
accessing a machine learning model trained to predict a motion field from a pair of radiological images captured from the same patient at different times, training the accessed model comprising, for each of a plurality of training pairs of radiological images captured from the same patient at different times:
applying the machine learning model to first and second radiological images of the training pair to obtain a predicted motion field value;
applying a spatial transform to transform the first radiological image of the training pair using the predicted motion field value;
comparing the transformed first radiological image of the training pair to the second radiological image of the training pair to obtain a loss metric value;
determining a region of interest segmentation mask against the first and second radiological images of the training pair;
applying a contour transform to transform the first radiological image of the training pair using the predicted motion field value and the region of interest segmentation mask; and
comparing the contour-transformed first radiological image of the training pair to the second radiological image of the training pair to obtain a contour loss metric value;
adjusting the state of the machine learning model based on the loss metric value and the contour loss metric value;
applying the accessed model to the production pair of radiological images to produce a predicted motion field for the production pair of radiological images; and
determining a strain result for the distinguished patient using the predicted motion field for the production pair of radiological images.

22. The one or more instances of computer-readable media of claim 21, the method further comprising:
storing the determined strain result for the distinguished patient.

23. The one or more instances of computer-readable media of claim 21 wherein the radiological images are cardiac ultrasound images, and wherein the determined strain result for the distinguished patient is a cardiac strain result, the method further comprising:
storing the determined strain result for the distinguished patient.

24. The one or more instances of computer-readable media of claim 21, the method further comprising:
causing the determined strain result for the distinguished patient to be displayed.

25. The one or more instances of computer-readable media of claim 21, the method further comprising:
making a diagnostic inference for the distinguished patient based upon the determined strain result for the distinguished patient.

26. A method in a computing system, comprising:
training a machine learning model to predict the value of a motion field between a pair of radiological images captured from the same patient at different times, by:
for each of a plurality of training pairs of radiological images captured from the same patient at different times:
applying the machine learning model to first and second radiological images of the training pair to obtain a predicted motion field value;
applying a spatial transform to transform the first radiological image of the training pair using the predicted motion field value;
comparing the transformed first radiological image of the training pair to the second radiological image of the training pair to obtain a loss metric value;
determining a region of interest segmentation mask against the first and second radiological images of the training pair;
applying a contour transform to transform the first radiological image of the training pair using the predicted motion field value and the region of interest segmentation mask; and
comparing the contour-transformed first radiological image of the training pair to the second radiological image of the training pair to obtain a contour loss metric value;
adjusting the state of the machine learning model based on the loss metric value and the contour loss metric value; and
storing the trained state of the machine learning model.

* * * * *